United States Patent [19]
Baker et al.

[11] Patent Number: 4,886,885
[45] Date of Patent: Dec. 12, 1989

[54] COMPOUND CONTAINING TETRAZOLYL GROUPS AND THEIR USE FOR TREATING ALLERGIES AND CARDIOVASCULAR DISEASE

[75] Inventors: Stephen R. Baker, Camberley; Alec Todd, Wokingham, both of England

[73] Assignee: Lilly Industries Limited, Basingstoke, England

[21] Appl. No.: 262,754

[22] Filed: Oct. 26, 1988

[30] Foreign Application Priority Data

Oct. 28, 1987 [GB] United Kingdom ............... 8725260

[51] Int. Cl.$^4$ .................. C07D 409/06; A61K 31/41
[52] U.S. Cl. ..................... 514/381; 548/252; 548/253; 549/74; 549/79
[58] Field of Search ................ 548/252, 253; 514/381

[56] References Cited

U.S. PATENT DOCUMENTS

| | | | |
|---|---|---|---|
| 4,031,236 | 6/1977 | Ahrens et al. | 424/275 |
| 4,513,005 | 5/1985 | Baker et al. | 514/451 |
| 4,663,332 | 5/1987 | Carson | 514/340 |
| 4,665,189 | 5/1987 | Baker et al. | 548/252 |
| 4,675,335 | 6/1987 | Baker et al. | 514/381 |
| 4,752,613 | 6/1988 | Floyd et al. | 514/438 |

FOREIGN PATENT DOCUMENTS

| | | |
|---|---|---|
| 123543 | 10/1984 | European Pat. Off. . |
| 228045 | 7/1987 | European Pat. Off. . |
| 2144422 | 3/1985 | United Kingdom . |
| 2168704 | 6/1986 | United Kingdom . |
| 2170204 | 7/1986 | United Kingdom . |
| 2184121A | 7/1987 | United Kingdom . |

*Primary Examiner*—David B. Springer
*Attorney, Agent, or Firm*—Robert A. Conrad; Leroy Whitaker

[57] ABSTRACT

A pharmaceutical compound of the formula:

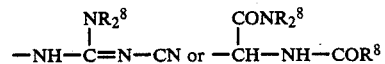

(I)

in which $R^1$ is $C_{7-20}$ alkyl, $C_{7-20}$ alkenyl or $C_{7-20}$ alkynyl, the alkyl, alkenyl or alkynyl group being optionally substituted by phenyl or substituted phenyl and the alkenyl and alkynyl groups containing 1 to 3 unsaturated bonds, $R^2$ is (i) optionally substituted phenyl, (ii) $C_{1-10}$ alkyl optionally substituted by one or more substituents selected from optionally protected hydroxyl, optionally protected carboxyl, nitrile, optionally protected tetrazolyl, —$COR^4$ where $R^4$ is $C_{1-14}$ alkyl, $C_{1-4}$ alkoxy, an optionally protected amino acid residue or —$NR_2^5$ where each $R^5$ is hydrogen or $C_{1-4}$ alkyl, and —$NHR^6$ where $R^6$ is hydrogen, a protecting group, an optionally protected amino acid residue, $C_{1-4}$ alkyl or —$COR^7$ where $R^7$ is $C_{1-4}$ alkyl or $C_{1-4}$ alkoxy, or (iii) $C_{1-10}$ alkyl substituted with a group selected from $$\begin{array}{cc} NR_2^8 & CONR_2^8 \\ | & | \\ -NH-C=N-CN \text{ or } & -CH-NH-COR^8 \end{array}$$

where each $R^8$ is hydrogen or $C_{1-4}$ alkyl, and $R^3$ is hydrogen, carboxyl, $C_{2-5}$ alkoxycarbonyl, $C_{1-4}$ alkyl, $C_{1-4}$ alkoxy, hydroxyl, optionally protected tetrazolyl, halo, trifluoromethyl, nitrile, nitro and —$CONR_2^9$ where each $R^9$ is hydrogen or $C_{1-4}$ alkyl; and salts thereof.

8 Claims, No Drawings

COMPOUND CONTAINING TETRAZOLYL GROUPS AND THEIR USE FOR TREATING ALLERGIES AND CARDIOVASCULAR DISEASE

This invention relates to organic compounds and their use as pharmaceuticals.

The compounds of the invention have the formula

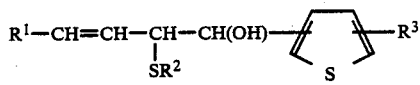
(I)

in which $R^1$ is $C_{7-20}$ alkyl, $C_{7-20}$ alkenyl or $C_{7-20}$ alkynyl, the alkyl, alkenyl or alkynyl group being optionally substituted by phenyl or substituted phenyl and the alkenyl and alkynyl groups containing 1 to 3 unsaturated bonds, $R^2$ is (i) optionally substituted phenyl, (ii) $C_{1-10}$ alkyl optionally substituted by one or more substituents selected from optionally protected hydroxyl, optionally protected carboxyl, nitrile, optionally protected tetrazolyl, —$COR^4$ where $R^4$ is $C_{1-4}$ alkyl, $C_{1-4}$ alkoxy, an optionally protected amino acid residue or —$NR_2^5$ where each $R^5$ is hydrogen or $C_{1-4}$ alkyl, and —$NHR^6$ where $R^6$ is hydrogen, a protecting group, an optionally protected amino acid residue, $C_{1-4}$ alkyl or —$COR^7$ where $R^7$ is $C_{1-4}$ alkyl or $C_{1-4}$ alkoxy, or (iii) $C_{1-10}$ alkyl substituted with a group selected from

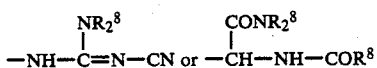

where each $R^8$ is hydrogen or $C_{1-4}$ alkyl, and $R^3$ is hydrogen, carboxyl, $C_{2-5}$ alkoxycarbonyl, $C_{1-4}$ alkyl, $C_{1-4}$ alkoxy, hydroxyl, optionally protected tetrazolyl, halo, trifluoromethyl, nitrile, nitro and —$CONR_2^9$ where each $R^9$ is hydrogen or $C_{1-4}$ alkyl; and salts thereof.

The compounds of the invention, in unprotected form, have been shown to be pharmacologically active in tests which demonstrate their antagonist effect on leukotriene receptors and indicate their use in the treatment of allergic disorders.

In the above general formula when $R^1$ is alkyl it can be branched or unbranched and preferably contains from 8 to 13 carbon atoms. Similarly when $R^1$ is alkenyl or alkynyl it can be branched or unbranched and preferably contains 7 to 13 carbon atoms. An alkenyl group can contain one or two triple bonds but preferably it comprises solely 1 to 3 double bonds. Preferred alkenyl groups are of the formula $R^{10}CH=CH—$ where $R^{10}$ is $C_{7-11}$ alkyl or $CH_3(CH_2)_nCH=CH—CH_2—CH=CH—$ where n is 0 to 4. It will be appreciated that the double bonds give rise to cistrans isomeric forms and two example of the group $R^1—CH=CH—$ are:

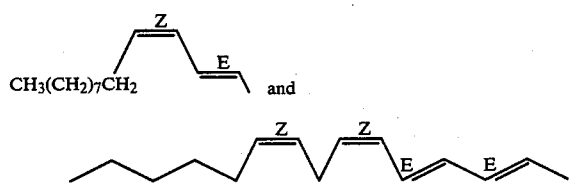

When $R^1$ is substituted it is substituted by an optionally substituted phenyl ring, preferably phenyl itself, or a phenyl group substituted with one or more, preferably 1 to 3, substituents selected from $C_{1-4}$ alkyl, especially methyl, $C_{1-4}$ alkoxy, especially methoxy and ethoxy, hydroxy, nitro, cyano, halo, especially chloro, trifluoromethyl, carboxyl, tetrazolyl and —$CONH_2$. When $R^1$ is substituted it is preferably an alkenyl group and a preferred value is the terminally substituted alkenyl group ω-phenyl.

With regard to $R^2$, this can be a $C_{1-10}$ alkyl group, preferably $C_{1-6}$ alkyl, and optionally substituted by one or more, preferably 1 to 3, substituents as defined above. The substituent can be, —$COR^4$ or —$NHR^6$ where $R^4$ and $R^6$ are amino acid residues. Such amino acid residues can be optionally protected by a conventional protecting group and can be derived from any of the commonly occurring amino acids. In the case of $R^4$ the residue is preferably derived from glycine having the value —$NHCH_2COOH$ and in the case of $R^6$ it is preferably derived from aspartic acid or glutamic acid, having the values —$COCH_2CH(NH_2)COOH$ and —$COCH_2CH_2CH(NH_2)COOH$, respectively.

Preferably $R^2$ is an alkyl group substituted with 1 to 3 substituents selected from carboxyl, nitrile, tetrazolyl, and —$COR^4$ where $R^4$ is —$NR_2^5$ or $C_{1-4}$ alkoxy.

A particularly preferred value of $R^2$ is of the following formula:

—$(CH_2)_xR^{11}$ 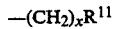

where x is 1 to 5 and $R^{11}$ is carboxyl, nitrile, —$CONH_2$ or tetrazolyl. Most preferred are groups in which x is 2 and/or $R^{10}$ is carboxyl or tetrazolyl.

As mentioned above, $R^2$ can be optionally substituted phenyl and it can be any of the values defined above when $R^1$ bears an optionally substituted phenyl group. Preferably the phenyl ring is substituted with 1 to 3 substitutents selected from carboxyl, tetrazolyl and —$CONH_2$, and especially a single carboxyl substituent.

As defined above, the group $R^3$ can be hydrogen, carboxyl, $C_{1-5}$ alkoxycarbonyl, $C_{1-4}$ alkyl, $C_{1-4}$ alkoxy, hydroxyl, optionally protected tetrazolyl, halo, trifluoromethyl, nitrile, nitro and —$CONR_2^9$ where each $R^9$ is hydrogen or $C_{1-4}$ alkyl. The tetrazolyl group is preferably 1H-tetrazol-5-yl. It is most preferred that the substituent be nitrile, —$CONH_2$, tetrazolyl or carboxyl, acid substituents such as tetrazolyl and carboxyl being best of all. Maximum activity results when the hydrocarbyl chain and $R^3$ substituent are attached at the 2- and 5- positions respectively.

In the above general formulae $C_{1-4}$ alkyl means a straight or branched chain alkyl group, for example, methyl, ethyl, propyl, isopropyl, butyl, isobutyl and tertiary butyl, and is preferably methyl or ethyl. Similarly a $C_{1-4}$ alkoxy group is any such alkyl group attached through oxygen to the appropriate moiety, and alkoxycarbonyl is a group of the form ROCO— where R is a $C_{1-4}$ alkyl group as described above.

When substituents on the compound of formula (I) require protection during preparation they may be protected by conventional protecting groups. Compounds with such protected carboxyl, amino acid residues, amino, hydroxyl and tetrazolyl groups are included in the scope of the invention, though the preferred compounds with optimum biological properties are the unprotected compounds derived from them. Carboxyprotecting groups are the well known ester forming groups used for the temporary protection of acidic carboxylic acid groups. Examples of such groups which have general use are readily hydrolysable groups such as arylmethyl groups, haloalkyl groups, trialkylsilyl groups, alkyl groups, and alkenyl groups. Other carboxy protecting groups are those described by E. Haslam in Protective Groups in Organic Chemistry, Chapter 5. The amino-protecting groups that can be employed in the preparation of the compounds of the invention are also conventional protecting groups. Illustrative of such groups are trihaloacetyl groups especially trifluoroacetyl. Such groups are well known in the art and are discussed, for example, in Peptide Synthesis by M. Bodansky, Y. S. Klausner and M. A. Ondetti, Second Edition (1976) John Wiley & Sons. Any free hydroxy groups present in the compound of the invention may likewise be protected if needed. For example, a hydroxy group on the $R^2$ group of a compound of the formula I, can be protected with a conventional labile ether forming protecting group such as an ether formed with dihydropyran or methylvinyl ether, or by esters formed with the lower alkyl carboxylic acids such as formic, acetic or propionic, or such halogenated acids, for example, chloroacetic acid, dichloroacetic acid or $\beta,\beta$-dichloropropionic acid. Furthermore, it is usually necessary to protect any tetrazolyl group during the process of preparation, and suitable and well known protecting groups for this purpose include the trityl and benzhydryl groups formed by reaction with the appropriate halide in the presence of base for example by reacting the tetrazolyl reactant with trityl chloride and triethylamine. In addition substituted trityl, substituted benzhydryl and optinally substituted benzyl may also be used as tetrazolyl protecting groups. Such groups are substituted on the phenyl ring with substituents such as listed above as suitable for optionally substituted phenyl. Protecting groups for the tetrazolyl radical are discussed in Advances in Heterocyclic Chemistry, Academic Press, 1977, vol. 21, pages 323 to 435.

When the compound of formula (I) bears an acidic function, base addition salts can be prepared and these are to be regarded as part of the present invention. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, calcium hydroxide, methylamine, diethylamine, ethylene diamine, cyclohexylamine and ethanolamine. The potassium and sodium salt forms together with other pharmaceutically acceptable salts are particularly preferred, but it is to be understood that other non-pharmaceutical salts are involved in the invention since they may be useful for identification, characterisation or purification of the free compound.

When the compound of formula (I) has a basic function, acid addition salts can be prepared and these are included in the present invention. Examples of such salts are those derived from, preferably non-toxic, inorganic acids such as for example hydrochloric acid, nitric acid, phosphoric acid, sulfuric acid and nitric acid, as well as salts derived from, preferably non-toxic, organic acids such as aliphatic mono- and di-carboxylic acids, phenyl-substituted alkanoic acids, hydroxyalkanoic acids, aromatic acids, and aliphatic and aromatic sulfonic acids.

It will be appreciated that the compounds of formula (I) possess chiral centres at the carbon atoms bearing the hydroxyl and $SR^2$ groups and, accordingly, stereoisomeric forms exist R,R; S,S; S,R, the most preferred being 1S, 2R. Other chiral centres are also possible, depending on the nature of the various substituents, which may lead to further stereoisomeric forms. Furthermore, the compounds exhibit cis-trans isomeric forms. All such stereoisomers, and racemic mixtures thereof, are included within the scope of the invention. Isomers can be isolated from racemic mixtures by conventional methods such as by the preparation of diastereoisomers with subsequent liberation of the enantiomers or, alternatively, can be prepared by methods devised to give the pure isomer.

A particular group of compounds according to formula (I) are as follows:

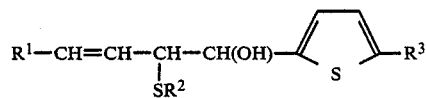

in which $R^1$ is $C_{7-20}$ alkyl or $C_{7-20}$ alkenyl containing 1 to 3 double bonds, $R^2$ is of the formula $-(CH_2)_xR^{11}$ where x is 1 to 5 and $R^{11}$ is carboxyl or tetrazolyl and $R^3$ is nitrile, carboxyl or tetrazolyl; and salts thereof. Of these compounds the preferred are those in which $R^1$ is of the formula $R^{10}CH=CH-$ where $R^{10}$ is $C_{7-11}$ alkyl or $CH_3(CH_2)_nCH=CH-CH_2-CH=CH-$ and n is 0 to 4.

The most preferred group of compounds are of the formula

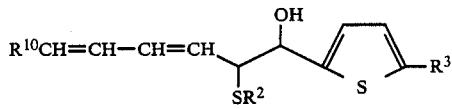

$R^{10}$ is $C_{7-11}$ alkyl, $R^2$ is $-(CH_2)_2R^{11}$ where $R^{11}$ is carboxyl or tetrazolyl, and $R^3$ is carboxyl or tetrazolyl; and salts thereof.

The invention also includes a process for producing a compound of formula (I) above which comprises reacting a compound of formula

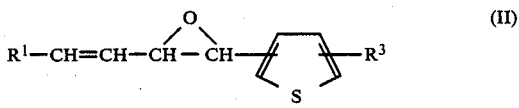

in which $R^1$ and $R^3$ are as defined above, with a thiol of formula $R^2SH$, in which $R^2$ is as defined above, optionally by removal of any protecting group, or by interconversion of an $R^3$ group.

The reaction of compound of formula (II) with thiol is preferably carried out in an inert organic solvent such as an alcohol, for example methanol, in the presence of a base such as a triethylamine and at a temperature of from 0° C. to 50° C. Thiol reactants containing a potential anion, especially if it is sterically close to the thiol group, are desirably protected before reaction.

It will be appreciated that it may be desired to remove any protecting groups attached to the product of the reaction. Such reactions can readily be carried out by use of a base in an inert organic solvent, such as for example, lithium hydroxide in tetrahydrofuran, or potassium carbonate in methanol, at a temperature of from 0° C. to 80° C., or by use of acid such as hydrochloric acid for removal of protecting groups from tetrazolyl, or by reduction in the case of protected amino groups, by well known procedures described for example in the authorities referred to above.

Also it will be appreciated that the $R^3$, group can be interconverted to other values. It is often preferred, depending on the nature of the group, that such interconversions are carried out after reaction of compound of formula (II) with thiol.

For example, compounds in which $R^3$ is $C_{2-5}$ alkoxycarbonyl or in which $R^2$ bears such a group can be converted to the corresponding free carboxyl by hydrolysis by means of base in water and with an inert organic co-solvent, such as for example, lithium hydroxide in tetrahydrofuran. Such methods are well known in the art. Conversely, compounds in which $R^3$ is $C_{2-5}$ alkoxycarbonyl or $R^2$ has such a group can be prepared from the free acid by esterification of the free carboxyl group with the appropriate alcohol or by treatment with alkyl halide in the presence of base. Salts of the free acid can, of course, be prepared simply by reaction with alkali.

Compounds in which $R^3$ is $-CONR_2^9$ or $R^2$ bears a $-CONR_2^5$ group can be prepared by reacting a compound with an appropriate alkoxycarbonyl substituent with ammonia or the appropriate amine of formula $R_2^9NH$ or $R_2^5NH$, respectively, or they can be prepared by the reaction of an amine of formula $R_2^9NH$ or $R_2^5NH$ with the appropriate acyl chloride, which can in its turn be derived from the free carboxyl derivative by the reaction of thionyl chloride. Such reactions are well known in the art.

Compounds in which $R^3$ is a nitrile group or $R^2$ has such a group can be prepared by dehydration of the appropriate amide ($-CONH_2$), a convenient dehydrating agent being, for example, a mixture of triphenylphosphine and carbon tetrachloride.

Compounds in which $R^3$ is tetrazolyl or $R^2$ has such a group can be prepared by reaction of the cyano derivative prepared as above with, for example sodium azide and ammonium chloride in dimethylformamide. Salts can be prepared from the tetrazolyl derivatives by the addition of base according to standard techniques.

It will be appreciated that the steps of reduction to provide the saturated $R^1$ substituents, oxidation to provide sulphones and sulphoxides, removal of protecting group or interconversion of groups, can be carried out in whatever sequence best suits convenience and the aim of maximising yield.

The reactants of formula $R^2SH$ are known compounds or can be prepared by methods of a type well known in the art. When they bear amino, carboxyl or hydroxyl groups the reaction may benefit in yield if these groups are first protected, but such initial protection is by no means necessary in all cases.

Compounds of formula (II), and their salts, in which $R^1$ is optionally substituted alkenyl or alkynyl are novel and are included as part of the present invention. They may be prepared by the Wittig reaction of a phosphonium salt of formula $R^1CH_2P^+Ph_3Br^-$, in the presence of a base such as butyl lithium, with an aldehyde of formula (III) or (IV)

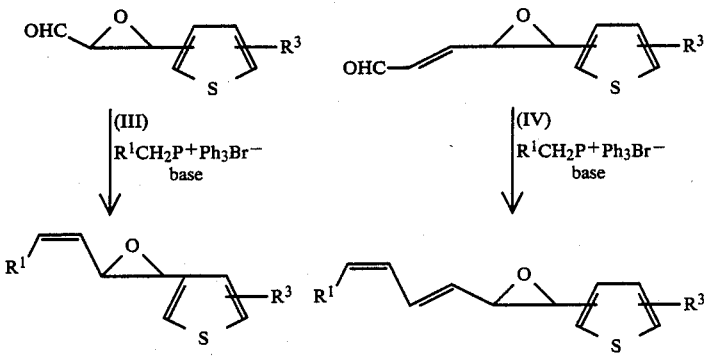

The reaction is generally carried out in an inert organic solvent such as for example, tetrahydrofuran, at a temperature of from $-80°$ C. to 0° C.

Compounds of formula (III) may be prepared from known intermediates by, for example, two principal routes. Firstly, they may be prepared, as racemic mixtures, by oxidation with, for example, hydrogen peroxide and sodium hydrogen carbonate in methanolic solution, of an aldehyde of the formula

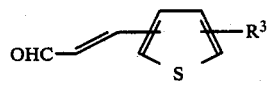

and, in its turn, aldehyde of formula (III) may be converted to one of formula (IV) by reaction with formylmethylenetriphenylphosphorane.

Alternatively, the compounds of formula (III) may be prepared by oxidation of an epoxy alcohol of the formula

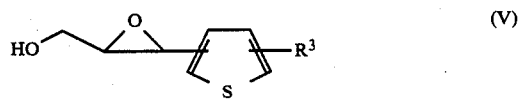

(V)

with an oxidising agent such as, for example, chromium trioxide in pyridine. Compounds of formula (V) can be prepared in stereospecific form and since the steric configuration is retained on oxidation to provide the aldehyde of formulae (III) and, ultimately, of formula (IV), this route can be employed to provide stereospecific compounds of formula (I).

Compounds of formula (V) are prepared from the allyl alcohol

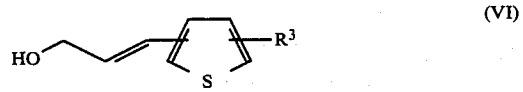

(VI)

using as epoxidising agent a reagent such as m-chloroperbenzoic acid, or if the enantiomeric form is desired by the use of titanium isopropoxide-t-butyl hy- The following scheme gives examples of the way in which preferred compounds of the invention may be prepared:

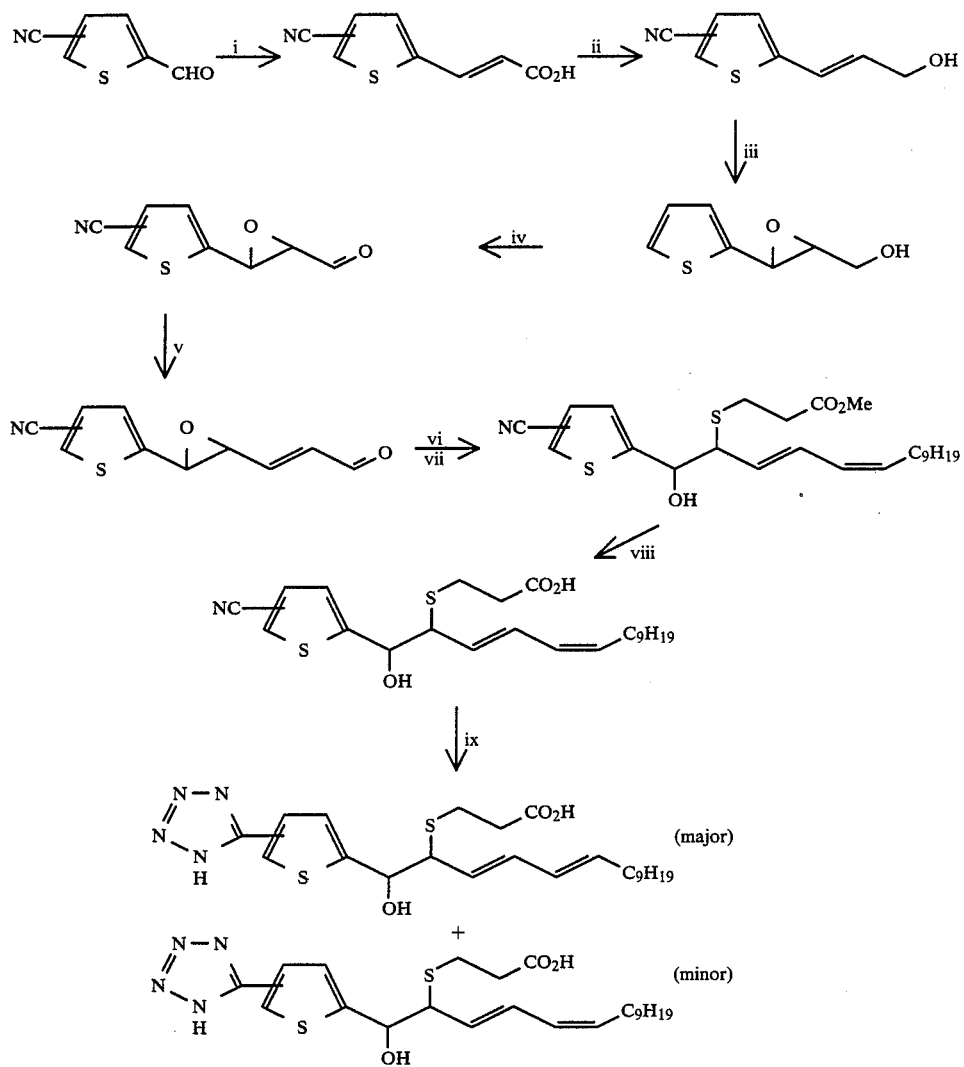

Key:
(i) CH₂(CO₂H)₂, pyridine
(ii) (COCl)₂: NaBH₄/Al₂O₃
(iii) MCPBA
(iv) (COCl)₂, DMSO, or CrO₃, pyridine
(v) Ph₃P=CHCHO
(vi) C₁₀H₂₁P⁺Ph₃Br⁻, NaN/SiMe₃)₂
(vii) HS(CH₂)₂CO₂Me, Et₃N
(viii) K₂CO₃
(ix) NaN₃, Et₃N.HCl droperoxide in the presence of L or D diethyl tartrate which yields the S,S or R,R epoxide, according to procedures described in European Pat. Nos. 0 046 033 and 0 197 766. When the Z olefin is used as starting material, the appropriate S,R and R,S stereoisomers result. Compounds of formula (VI) can be prepared from the appropriate aldehyde via a sequence of reactions involving reaction with malonic acid to provide the cinnamic acid derivative, treatment with oxalyl chloride to give the acid chloride, and reduction with a reagent such as lithium tri-t-butoxyaluminohydride.

The compounds of the present invention are pharmacologically active, being leukotriene antagonists as shown by the in vitro test on guinea pig ileum segments at concentrations of from 10 ng to 50 μg, according to the method of Schild (1947) Brit. J. Pharm. 2, 197–206 (the unprotected compounds of formula (I) described in the following Examples exhibited an IC$_{50}$ against LTD$_4$ of less than $10^{-5}$ molar). Also compounds of the invention are active in the in vivo Guinea Pig Pulmonary Function Test of Austen and Drazen (1974) J. Clin. Invest. 53 1679–1685 at intravenous dosage levels of from 0.05 μg to 5.0 mg/kg and in a modified "Herxheimer" test (Journal of Physiology (London) 117 251 (1952)) at doses of from 25 to 200 mg/kg. The "Herxheimer" test is based on an LTD$^4$-induced bronchospasm in guinea pigs which closely resembles an asthmatic attack in man.

The compounds are accordingly indicated for therapeutic use in the treatment of diseases in which leukotrienes are implicated. These include allergic reactions of the pulmonary system in which leukotrienes are thought to be causal mediators of bronchospasm, for example, in allergic lung disorders such as extrinsic asthma and industrial asthmas such as Farmers lung and Pigeon Fanciers lung, and in other inflammatory disorders, for example, associated with acute or chronic infectious diseases such as allergic skin diseases, ectopic and atopic eczemas, psoriasis, contact hypersensitivity and angioneurotic oedema, bronchitis and cystic fibrosis and rheumatic fever. Equally important, the compounds of the invention are indicated for use in cardiovascular diseases such as shock and ischaemic heart diseases for example coronary artery disease and myocardial infarction, cerebrovascular diseases, and renal diseases for example renal ischaemia.

Thus the invention also includes a pharmaceutical composition comprising a pharmaceutically acceptable diluent or carrier in association with a compound of formula (I) in unprotected form; or a pharmaceutically acceptable salt thereof.

The compounds may be administered by various routes, for examples by the oral or rectal route, topically or parenterally. The preferred method of administration is by inhalation, being usually employed in the form of a pharmaceutial composition. Such compositions are prepared in a manner well known in the pharmaceutical art and normally comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phoshpate, alginates, tragacanth, gelatin, syrup, methyl cellulose, methyl- and propyl- hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example, from 25 mg to 200 mg. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances includeing the condition to be treated, the choice of compound to be administered and the chosen route of administration, and therefore the above dosage ranges are not intended to limit the scope of the invention in any way.

The invention is illustrated by the following Examples. The structure of the compounds prepared was confirmed by I.R. and/or n.m.r. and/or mass spectra and the purity of the product was checked in most cases by HPLC. The involatile products were examined by mass spectrometry using the fast atom bombardment (FAB) technique in the negative ion mode. Significant [M-H]$^-$ ions (and characteristic fragment ions) were observed.

EXAMPLE 1

Rel-(1S,2R)-5-{5-[2-(2-carboxyethylthio)-1-Hydroxypentadeca-3(E),-5(E)-dienyl]-thien-2-yl}-1H-tetrazole (a) 3-(5-Cyano-2-thiophenyl)-propenoic acid A stirred solution of 5-cyano-2-thiophene carboxaldehyde (3.3 g) and malonic acid (2.5 g) in pyridine (35 ml) and piperidine (0.7 ml) was heated under reflux for 2 hours adding further malonic acid (1.3 g) after 1 hour. The solution was evaporated and the residue was stirred with M hydrochloric acid solution (100 ml) to give a pale solid which was washed with water and dried, m.p. ca 260° C. (subliming).

(b) 3-(5-Cyano-2-thiophenyl)-2-propenol

Dimethylformamide (0.1 ml) was added to a stirred suspension of 3-(5-cyano-2-thiphenyl)-propenoic acid (3.7 g) in dry ether (100 ml) and dry tetrahydrofuran (100 ml) containing oxalyl chloride (2.2 ml). The mixture was stirred for 2 hours then the clear solution was decanted from a little dark tar and evaporated to give the crude acid chloride as a pale solid. A solution of this acid chloride in ether (50 ml) and tetrahydrofuran (50 ml) was added rapidly to a stirred suspension of sodium borohydride doped alumina (3.5 g sodium borohydride on 35 g alumina) in ether (100 ml) with cooling to keep at 15°–20° C. The mixture was stirred for 1 hour and then filtered. The filtrate was evaporated and the residue was chromatographed on silica-gel eluting with ether to give the product as a pale solid.

(c) 3-(5-Cyano-2-thiophenyl) 2,3-oxidopropanol

Solid m-chloroperbenzoic acid (0.75 g) was added to a stirred solution of 3-(5-cyano-2-thiophenyl)-2-propenol (0.60 g) in dichloromethane (50 ml). The solution was stirred for 5 hours then washed with 10% sodium carbonate solution, dried and evaporated. The residue was chromatographed on silica gel, eluting with ether, to give the product as a pale solid.

(d) 3-(5-Cyano-2-thiophenyl) 2,3-oxidopropanol

A solution of dry dimethyl sulphoxide (0.29 ml) in dichloromethane (1 ml) was added dropwise to a stirred solution of oxalyl chloride (0.18 ml) in dichloromethane (4 ml) at ca. −60° C. under nitrogen. The solution was stirred for 5 minutes at −60° C. then a solution of 3-(5-cyano-2-thiophenyl)2,3-oxidopropanol (0.34 g) i dichloromethane (4 ml ) as added over 20 minutes. The cloudy mixture was stirred for a further 15 minutes at −60° C. and 5 minutes at −45° C. then triethylamine (0.7 ml) was added at −60° C. The mixture was allowed to warm to room temperature, washed with water, dried and evaporated to give the crude product as a dark tar.

(e) 5-(5-Cyano-2-thiophenyl)4,5-oxido-2-pentenal

A mixture of crude 3-(5-cyano-2-thiophenyl)2,3-oxidopropanol (348 mg) and formylmethylene triphenylphosphorane (473 mg) in benzene (10 ml) was stirred for 4 hours. The clear benzene solution was decanted from some insoluble dark tar and evaporated. The residue was extracted with ether and the extract re-evaporated. The pale residue was chromatographed as silica gel in 2:1 ether:hexane to give the product as a pale solid, m.p. 85° C.

(f) rel (1S,2R)-5-[2-(2-Methoxycarbonylethylthio)-1-hydroxypentadeca-3(E)5(Z)-dienyl]thiophene-2-carbonitrile Solid sodium bis (trimethylsilyl) amide (75 mg) was added to a stirred solution of n-decyl-triphenylphosphonium bromide (145 mg) in dry tetrahydrofuran (6 ml) under nitrogen. The orange mixture was stirred for 2 hours then cooled to −75° C. whilst a solution of 5-(5-cyano-2-thiophenyl)4,5-oxido-2-pentanol (61.4 mg) in dry tetrahydrofuran (3 ml) was added dropwise. The brown mixture was stirred for 1 hour at −75° C., allowed to warm to room temperature and evaporated. The residue was extracted with ether and the extract was evaporated to give crude 5-(1,2-oxido-pentadeca-3(E)5(Z)-dienyl)thiophene-2-carbonitrile as a dark gum.

A solution of this crude epoxide, methyl 3-mercaptopropionate (32 μl) and triethylamine (67 μl) in dry methanol (1 ml) was stirred under nitrogen for 16 hours. The solution was evaporated and the residue was chromatographed on silica gel eluting with 1:1 ether:hexane to give the product as a pale oil.

(g) rel-(1S,2R)-5-{5-[2-(2-Carboxyethylthio)-1-hydroxy pentadeca-3(E)5(E)-dienyl]-thien-2-yl}-1H-tetrazole A solution of rel (1S,2R)-5-[2-(2-methoxycarbonylethylthio)-1-hydroxypentadeca 3(E)5(Z)-dienyl]thiophene-2-carbonitrile (42 mg) in methanol (10 ml) and 0.5M potassium carbonate solution (10 ml) was stirred for 16 hours. The solution was concentrated to ca half volume, diluted with water, acidified and extracted with ether. The extract was dried and evaporated to give crude rel(1S,2R)-5-[2-(2-carboxyethylthio)-1-hydroxypentadeca-3(E)5(Z)dienyl]thiophene-2-carbonitrile as a pale gum.

A stirred mixture of this nitrile (22.4 mg), sodium azide (32 mg) and triethylamine hydrochloride (74 mg) in dry dimethylformamide (1 ml) was heated at 120° C. for 2 hours under nitrogen. The cooled mixture was filtered and the filtrate was diluted with dilute hydrochloric acid and extracted with ether. The extract was dried and evaporated and the residue was purified by reverse-phase high pressue liquid chromatography (RPHPLC) using a 75 methanol:25 water:0.1 acetic acid mixture as eluant, to give the title compound as a pale gum.

EXAMPLE 2 rel-(1S,2R)-5-{4-[2-(2-Carboxyethylthio)-1-hydroxy pentadeca-3(E),5(E)-dienyl]thien-2-yl}1H-tetrazole (a) 3-(4-Cyano-2-thiophenyl)-propenoic acid was prepared by the method described in Example 1a), m.p. ca 260° C. (subliming).

(b) 3-(4-Cyano-2-thiophenyl)-2-propenol was prepared by the method described in Example 1b).

(c) 3-(4-Cyano-2-thiophenyl)-2,3-oxidopropanol was prepared by the method described in Example 1c).

(d) 5-(4-Cyano-2-thiophenyl)-4,5-oxido-2-pentenal

Chromium trioxide (8.3 g) was added to a stirred solution of pyridine (13.3 ml) in dichloromethane (300 ml) at 5° C. The mixture was stirred for 10 minutes warming to 13° C. then a solution of 3-(4-cyano-2-thiophenyl)-2,3-oxidopropanol (3.0 g) in dichloromethane (30 ml) was added rapidly. The dark mixture was stirred for a further 45 minutes warming to 20° C. and then filtered through a short column of Florisil. The colourless filtrate was evaporated to give crude 3-(4-cyano-2-thiophenyl)2,3-oxidopropanol as a pale oil.

A solution of this product and formylmethylene triphenylphosphorane (3.0 g) in toluene (200 ml) was stirred for 2 hours and evaporated. The residue was extracted with ether and the extract was evaporated and the residue was chromatographed on silica gel in 2:1 ether:hexane to give the product as a pale solid.

(e) rel (1S,2R)-4-[2-(2-Methoxycarbonylethylthio)-1-hydroxypentadeca-3(E)5(Z)-dienyl]thiophene-2-carbonitrile was prepared by the methods described in Example 1f).

(f) rel (1S,2R)-4-[2-(2-Carboxyethylthio)-1-hydroxypentadeca-3(E)5(Z)-dienyl]thiophene-2-carbonitrile A mixture of rel (1S,2R)5-[2-(2-methoxycarbonylethylthio)-1-hydroxypentadeca-3(E)5(Z)-dienyl]thiophene-2-carbonitrile (1.1 g) methanol (100 ml) and 0.5 m) potassium carbonate solution (200 ml) was stirred for 24 hours adding further methanol (100 ml) after 16 hours to give a clear solution. The solution was concentrated to ca 100 ml, washed with ether, acidified and extracted with ether. The extract was dried and evaporated to give the product as a pale gum.

(g) rel (1S,2R)-4-{4[2-(2-Carboxyethylthio)-1-hydroxy pentadeca-3(E)5(E)-dienyl]thien-2-yl}1H-tetrazole was prepared by the method described in Example 1g). The 3(E)5(Z) isomer was also isolated from the chromatography.

The active compounds of the invention are preferably employed in salt form and the following formulations are given by way of example:

EXAMPLE 3

| Aerosol | |
|---|---|
| Active ingredient | 10 mg |
| Ethanol | 50 mg |
| Dichlorodifluoromethane (Propellant 12) | 658 mg |
| Dichlorotetrafluoroethane (Propellant 114) | 282 mg |

The active ingredient is dissolved in the ethanol. The concentrate is filled into extruded aluminium cans for inhalation aerosols. The cans are degassed with propellant 12 and sealed with an appropriate metered dose valve. The volume of product expelled per actuation is 50 or 100 μl equivalent to 0.5–1 mg active ingredient.

EXAMPLE 4

| Soft gelatin capsule | |
| --- | --- |
| Each soft gelatin capsule contains: | |
| Active ingredient | 150 mg |
| Arachis oil | 150 mg |

After mixing together, the blend is filled into soft gelatin capsules using the appropriate equipment.

EXAMPLE 5

| Hard gelatin capsule | |
| --- | --- |
| Each capsule contains: | |
| Active ingredient | 50 mg |
| PEG (RTM) 4000 | 250 mg |

The PEG 4000 is melted and mixed with the active ingredient. Whilst still molten the mixture is filled into capsule shells and allowed to cool.

What is claimed is:

1. A compound of the formula

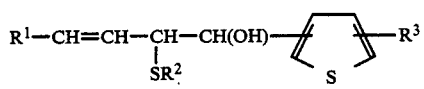 (I)

in which $R^1$ is $C_{7-20}$ alkyl, $C_{7-20}$ alkenyl or $C_{7-20}$ alkynyl, the alkyl, alkenyl or alkynyl group being optionally substituted by phenyl or substituted phenyl and the alkenyl and alkynyl groups containing 1 to 3 unsaturated bonds, $R^2$ is (i) optionally substituted phenyl, (ii) $C_{1-10}$ alkyl optionally substituted by one or more substituents selected from optionally protected hydroxyl, optionally protected carboxyl, nitrile, optionally protected tetrazolyl, $-COR^4$ where $R^4$ is $C_{1-4}$ alkyl, $C_{1-4}$ alkoxy, an optionally protected amino acid residue or $-NR_2^5$ where each $R^5$ is hydrogen or $C_{1-4}$ alkyl, and $-NHR^6$ where $R^6$ is hydrogen, a protecting group, an optionally protected amino acid residue, $C_{1-4}$ alkyl or $-COR^7$ where $R^7$ is $C_{1-4}$ alkyl or $C_{1-4}$ alkoxy, or (iii) $C_{1-10}$ alkyl substituted with a group selected from $$-NH-\underset{\underset{NR_2^8}{|}}{C}=N-CN \quad \text{or} \quad -\underset{\underset{CONR_2^8}{|}}{CH}-NH-COR^8$$

where each $R^8$ is hydrogen or $C_{1-4}$ alkyl, and $R^3$ is hydrogen, carboxyl, $C_{2-5}$ alkoxycarbonyl, $C_{1-4}$ alkyl, $C_{1-4}$ alkoxy, hydroxyl, optionally protected tetrazolyl, halo, trifluoromethyl, nitrile, nitro and $-CONR_2^9$ where each $R^9$ is hydrogen or $C_{1-4}$ alkyl; and pharmaceutically acceptable salts thereof provided that $R^3$ is tetrazolyl and/or $R^2$ is $C_1-C_{10}$ alkyl substituted with tetrazolyl.

2. A compound of the formula

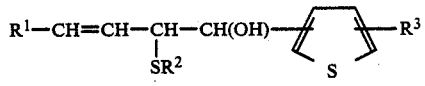

in which $R^1$ is an alkenyl group containing 7 to 13 carbon atoms, $R^2$ is $C_{1-10}$ alkyl substituted with carboxyl, nitrile, tetrazolyl, $-COR^4$ where $R^4$ is $C_{1-4}$ alkoxy or $-NR_2^5$ where each $R^5$ is hydrogen or $C_{1-4}$ alkyl, and $R^3$ is nitrile, $-CONH_2$, tetrazolyl or carboxyl; and pharmaceutically acceptable salts thereof provided that $R^3$ is tetrazolyl and/or $R^2$ is $C_1-C_{10}$ alkyl substituted with tetrazolyl.

3. A compound according to claim 2 in which $R^1$ is an alkenyl group of the formula $R^{10}CH=CH$ where $R^{10}$ is $C_{7-11}$ alkyl.

4. A compound according to claim 3 in which $R^2$ is $(CH_2)_xR^{11}$ where x is 1 to 5 and $R^{11}$ is carboxyl or tetrazolyl.

5. A compound of claim 1 of the formula

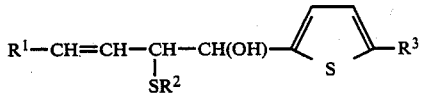

in which $R^1$ is $R^{10}CH=CH-$ where $R^{10}$ is $C_{7-11}$ alkyl, $R^2$ is $-(CH_2)_xR^{11}$ where x is 1 to 5 and $R^{11}$ is carboxyl or tetrazolyl, and $R^3$ is nitrile, carboxyl or tetrazolyl; and pharmaceutically acceptable salts thereof provided that $R^3$ is tetrazolyl and/or $R^2$ is $C_1-C_{10}$ alkyl substituted with tetrazolyl.

6. (1S,2R)-5-{5-[2-(2-Carboxyethylthio)-1-hydroxypentadeca-3(E)-5(E)-dienyl]-thien-2-yl}-1H-tetrazole.

7. A pharmaceutical formulation comprising a compound according to claim 1, or a pharmaceutically-acceptable salt thereof, together with a pharmaceutically-acceptable diluent or carrier therefor.

8. A method of treating an animal, including a human, suffering from or susceptible to an allergic disorder or cardiovascular disease, which comprises administering an effective amount of a compound of formula (I) as defined in claim 1, or a pharmaceutically-acceptable salt thereof.

* * * * *